United States Patent [19]

Monnier

[11] Patent Number: 4,549,563

[45] Date of Patent: Oct. 29, 1985

[54] GAS MIXERS

[75] Inventor: Jean-Pierre Monnier, Maurepas, France

[73] Assignee: L'Air Liquide, Societe Anonyme Pour l'Etude et l'Exploitation des Procedes Georges Claude, Paris, France

[21] Appl. No.: 507,066

[22] Filed: Jun. 23, 1983

[30] Foreign Application Priority Data

Jun. 29, 1982 [FR] France .................................. 82 11343

[51] Int. Cl.$^4$ ........................................... G05D 11/03
[52] U.S. Cl. ....................................... 137/100; 137/110; 137/510; 137/595; 128/203.14
[58] Field of Search ..................... 137/100, 625.18, 595, 137/510, 110, 513.7, 505.12, 98; 128/203.12, 203.14

[56] References Cited

U.S. PATENT DOCUMENTS

| | | | |
|---|---|---|---|
| 2,016,234 | 10/1935 | Hughes | 137/505.41 X |
| 2,245,210 | 6/1941 | McElwaine | 137/505.12 |
| 2,405,010 | 7/1946 | Bucknam | 137/505.38 |
| 2,935,084 | 5/1960 | Crawford et al. | 137/505.38 |
| 3,013,790 | 12/1961 | Anderson et al. | 137/510 X |
| 3,351,057 | 11/1967 | Goodyear et al. | 128/203.12 X |
| 3,511,270 | 9/1968 | Fehrenbach et al. | 137/510 X |
| 3,785,333 | 1/1974 | Warncke et al. | 137/557 |
| 4,325,349 | 4/1982 | Fehrenbach | 137/110 X |

FOREIGN PATENT DOCUMENTS

| | | | |
|---|---|---|---|
| 2706857 | 8/1978 | Fed. Rep. of Germany | 137/100 |
| 2028434 | 3/1980 | United Kingdom | 137/100 |
| 2041225 | 9/1980 | United Kingdom | 128/203.12 |

Primary Examiner—Martin P. Schwadron
Assistant Examiner—Stephen M. Hepperle
Attorney, Agent, or Firm—Young & Thompson

[57] ABSTRACT

A mixer for delivering a mixture of two gases $G_1$ and $G_2$ in proportions respectively and by volume of $X/100$ and $(100-X)/100$; $X/100$ not being allowed to be smaller than a particular value. Each gas circuit comprises a pipe provided with a cock for adjustment of the rate of flow and with a calibrated orifice selected in such manner that for an identical pressure P, the rates of flow of the gases through these orifices are in the ratio $X/(100-X)$, with devices for limiting the pressure of the gas $G_2$ to that of the gas $G_1$, as well as for limiting the pressure in both circuits. The invention is applicable to an oxygen-nitrous oxide mixer for anaesthetic purposes, in which the proportion of oxygen in the mixture supplied cannot drop below 25% and the flow rate of nitrous oxide cannot exceed a predetermined maximum.

6 Claims, 5 Drawing Figures

GAS MIXERS

BACKGROUND OF THE INVENTION

The present invention relates to a mixer for delivering a mixture of two gases $G_1$ and $G_2$ in proportions by volume of $X/100$ and $(100\ X)/100$ respectively, of the kind comprising a circuit for each of the said gases, connected to a circuit for the mixture.

There are special applications for which the lowest proportion of one gas by comparison with the other should be adhered to strictly, and this applies in the case of anaesthesia in which the safety of operation of the oxygen and nitrous oxide mixers represents an essential condition. The mixture supplied should contain a minimum of 21% of oxygen so that it is not hypo-oxidic.

It is an object of the invention to prevent or minimise delivery of a mixture containing less than $X/100$ of $G_1$ gas (oxygen), and to limit the flow rate of the gas $G_2$ (nitrous oxide) to a particular value notwithstanding the adjustment of the feed rates of the said gases.

SUMMARY OF THE INVENTION

To this end the invention proposes a mixer in which each of the aforesaid gas circuits comprises a pipe or duct connected to a source and is provided with a calibrated orifice selected in such manner than for an identical pressure P of both gases, the rates of flow of the said gases through these orifices are in the ratio of $X/(100-X)$ means being provided to limit the pressure of the gas $G_2$ to that of the gas $G_1$, as are means to limit the pressure in the two circuits and to allow passage of the gas $G_1$ drawn from its calibrated orifice starting at the said pressure.

The selection of the calibrated orifices to ensure that the rates of gas flow through the said orifices are in the ratio $X/(100-X)$ for an identical pressure of both gases; the circumstance that means are provided for limiting the pressure of the gas $G_2$ to the pressure of the gas $G_1$, and the fact of limiting the pressure of the gas $G_1$, have the result that the mixer in accordance with the invention always delivers a mixture containing a minimum of $X/100$ of the gas $G_1$ and limits the rate of flow of the gas $G_2$ to a particular value irrespective of the degree of opening of the flow rate control cocks.

According to another feature of the invention, the aforesaid limiting means comprises a pressure limiter provided with a diaphragm controlling the positioning of a valve in the duct of the gas $G_2$, the said diaphragm being exposed at one side to the pressure of the gas $G_1$ and at the other side to the pressure of the gas $G_2$. The pressure of the gas $G_2$ then cannot exceed the pressure of the gas $G_1$.

According to yet another feature of the invention, the aforesaid pressure limiting means comprise a release device incorporating a chamber in the circuit of the gas $G_1$ and a diaphragm exposed to the action of a calibrated spring and arranged for closing and opening a duct or passage connected to the circuit of the gas $G_1$ downstream of its calibrated orifice and leading into the aforesaid chamber.

This release device opens when the pressure of the gas $G_1$, representing a function of the rate of flow through the orifice 14, reaches the value determined by the force of the calibrated spring. This opening action limits the pressure of the gas $G_1$ and, as a consequence, the rate of flow of the gas $G_2$.

Other features and advantages of the invention will emerge from the following description.

BRIEF DESCRIPTION OF THE DRAWINGS

In order that the invention may be more clearly understood reference will now be made to the accompanying drawings, given by way of example only, which illustrate certain embodiments thereof and in which.

DESCRIPTION OF THE PREFERRED EMBODIMENTS

Figure 1:
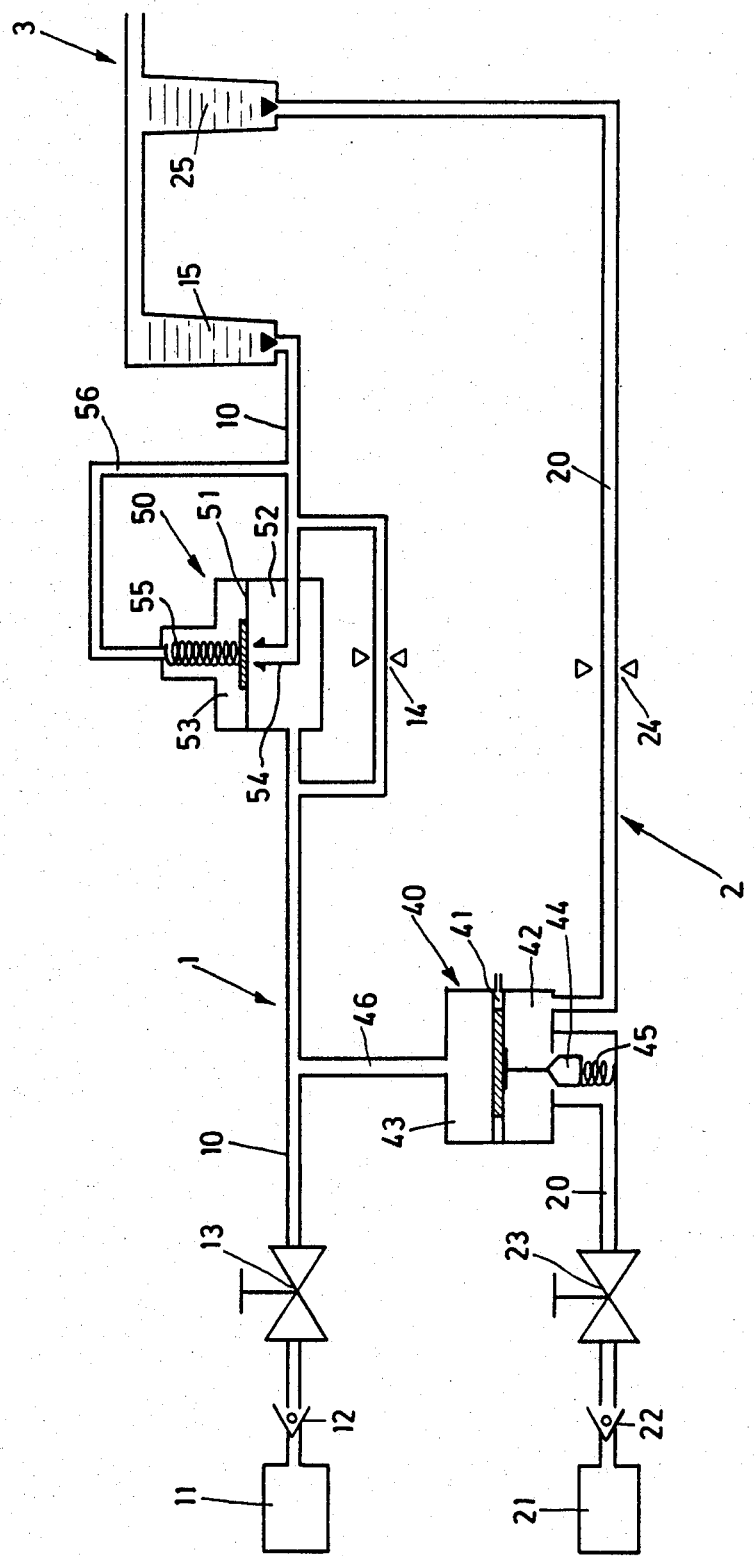
FIG. 1 is an illustration in diagrammatical manner of a mixer in accordance with the invention which is applicable in particular for producing an oxygen-nitrous oxide mixture for anaesthetic purposes.

According to the embodiment illustrated in FIG. 1, the mixer comprises a circuit for the gas $G_1$, a circuit for the gas $G_2$ and a circuit for the mixture of the two gases, these three circuits being denoted in a generalised manner by 1, 2 and 3 respectively.

The circuit 1 comprises a pipe 10 connected to a source 11 of the gas $G_1$ via a check valve 12, and a flow-rate control valve 13, and it has a calibrated orifice 14 and a rotary flow-meter 15 which serves the purpose of verifying the rate of flow of the gas $G_1$.

In similar manner, the circuit 2 comprises a pipe 20 connected to a source 21 of the gas $G_2$ via a check valve 22 and a flow-rate control valve 23, and it comprises a calibrated orifice 24 and a rotary flow-meter 25 serving the purpose of checking on the rate of flow of the gas $G_2$.

A pressure limiter 40 limits the pressure of the gas $G_2$ to that of the gas $G_1$. The limiter comprises a diaphragm 41 which divides the same internally into two chambers 42 and 43. The chamber 42 is connected in the pipe 20 of the gas $G_2$ and is provided with a valve 44 in unit with the diaphragm 41 and exposed to the action of a return spring 45 which tends to thrust the same into the closed position. The chamber 43 is connected via a pipe 46 to the pipe 10 of the gas $G_1$.

A release device 50 branched on the pipe 10 renders it possible to draw off the gas $G_1$ when the rate of flow of this latter exceeds a particular value, thereby keeping the pressure constant in circuit 1 starting from this rate of flow.

The release device 50 comprises a diaphragm 51 which divides it internally into a chamber 52 and a chamber 53. The chamber 52 is in direct communication with the circuit 10 and comprises a nozzle 54 connected to the said pipe 10. A calibrated spring 55 housed in the chamber 53 tends to thrust the diaphragm 51 against the nozzle or bleed 54 and consequently to close or open this latter depending on the pressure prevailing in circuit 1.

A pipe 56 connecting the chamber 53 of the release device to the pipe 10 downstream of the chamber 52 renders it possible to link the release device positively to the outflow pressure of the gas $G_1$ in such manner as to mitigate the effects of the utilisation pressure downstream of the mixer.

In the case of a mixer intended to derive an anaesthetic oxygen-nitrous oxide mixture (which should contain a minimum of 21% of oxygen as stated above), the invention proposes to prevent delivery of a mixture containing less than 25% of oxygen irrespective of the rate of flow of oxygen, and to limit the rate of flow of the nitrous oxide to 12 liters/min.

Figure 2:
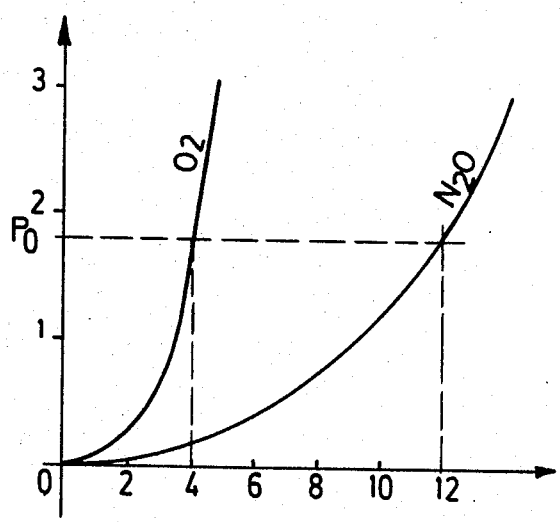
FIG. 2, illustrates the flow-rate/pressure characteristic for oxygen and nitrous oxide obtained with a mixer the two circuits of which are provided with calibrated orifices yielding flow rates in the ratio of 25% to 75% for an identical supply pressure.

In this case, the circuits 1 and 2 of FIG. 1 are the oxygen and the nitrous oxide circuits respectively, the mixing circuit 3 is connected to a consumer element, for example a respirator mask (not illustrated), and the calibrated orifices 14 and 24 are rated in such manner that for an identical pressure P, the rate of flow of nitrous oxide is at most equal to three times the rate of flow of oxygen. The variation of these rates of flow as a function of the pressure for orifices of this nature, is illustrated in FIG. 2.

Figure 3:
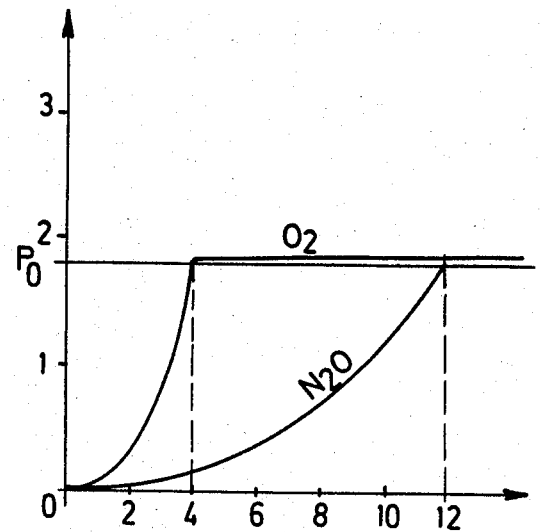
FIG. 3 illustrates the flow-rate/pressure characteristic of oxygen and nitrous oxide obtained with a mixer in accordance with the invention, FIGS. 4 and 5 respectively, show a first and second variant of the mixer according to FIG. 1.

The release device 40 controlled by the oxygen prevents the pressure of the nitrous oxide from exceeding the oxygen pressure. The calibrated spring 55 of the release device 50 is so rated that the diaphragm 51 clears the bleed 54 when the rate of flow of oxygen rises above 4 liters/min. Consequently, the pressure in the oxygen circuit and consequently in the nitrous oxide circuit, is limited to the value $P_o$ and the maximum rate of flow of the nitrous oxide amounts to 12 liters/min as illustrated in FIG. 3.

A mixer in accordance with the invention may have the following characteristics:
  calibrated orifice 14: diameter=0.45 mm allowing of
    a rate of flow of oxygen of 4 liters/min at 1.8 bar
  calibrated orifice 24: diameter=0.76 mm allowing of
    a rate of flow of nitrous oxide of 12 liters/min at 1.8 bar
  release device 50 set to 1.8 bar, in such manner as to limit the pressure in both circuits to the value $P_o$ (see FIG. 3): the rate of flow of nitrous oxide is thus limited to 12 liters/min.

It may be necessary to supply the patient with pure oxygen for a particular period at least, instead of with the conventional mixture of oxygen and nitrous oxide. A switching valve or "flush" valve 60 provided for this purpose has been illustrated in FIG. 4. The valve 60 comprises first and second chambers 61 and 62 in which are slide valves 63 and 64, respectively, provided with rods 63a and 64a and exposed to the action of return springs 65 and 66. The chamber 61 communicates with the pipe 30 of the mixing circuit or utilisation circuit 3 and comprises an orifice 67 in communication with the outside, whereas the chamber 62 communicates with the pipe 68 connected to the oxygen source 11. A pushbutton 69 acting on the rods 63a, 64a, renders it possible to cause the valves 63, 64 to slide against the action of the return springs 65, 66. The pipes 30 and 68 are connected to a consumer unit, for example a respiratory mask (not illustrated). The location of the pipes 30 and 68 and of the orifice 67 in the chambers 61 and 62 is arranged to provide a reversal in the supply of oxygen-nitrous oxide mixture and of pure oxygen depending on the position of the valves. When these assume the position shown by solid lines (normal position), the consumer unit is supplied with mixture only, whereas when they occupy the position illustrated by dotted lines (button 69 pushed in), the consumer unit is supplied with oxygen only, the mixture of oxygen and nitrous oxide escaping through the orifice 67. The valve 60 thus renders it possible to flush out the mixture and to replace the same by pure oxygen at a high rate of flow (exceeding 35 liters per minute) without simultaneous delivery of mixture and of oxygen.

Figure 4:
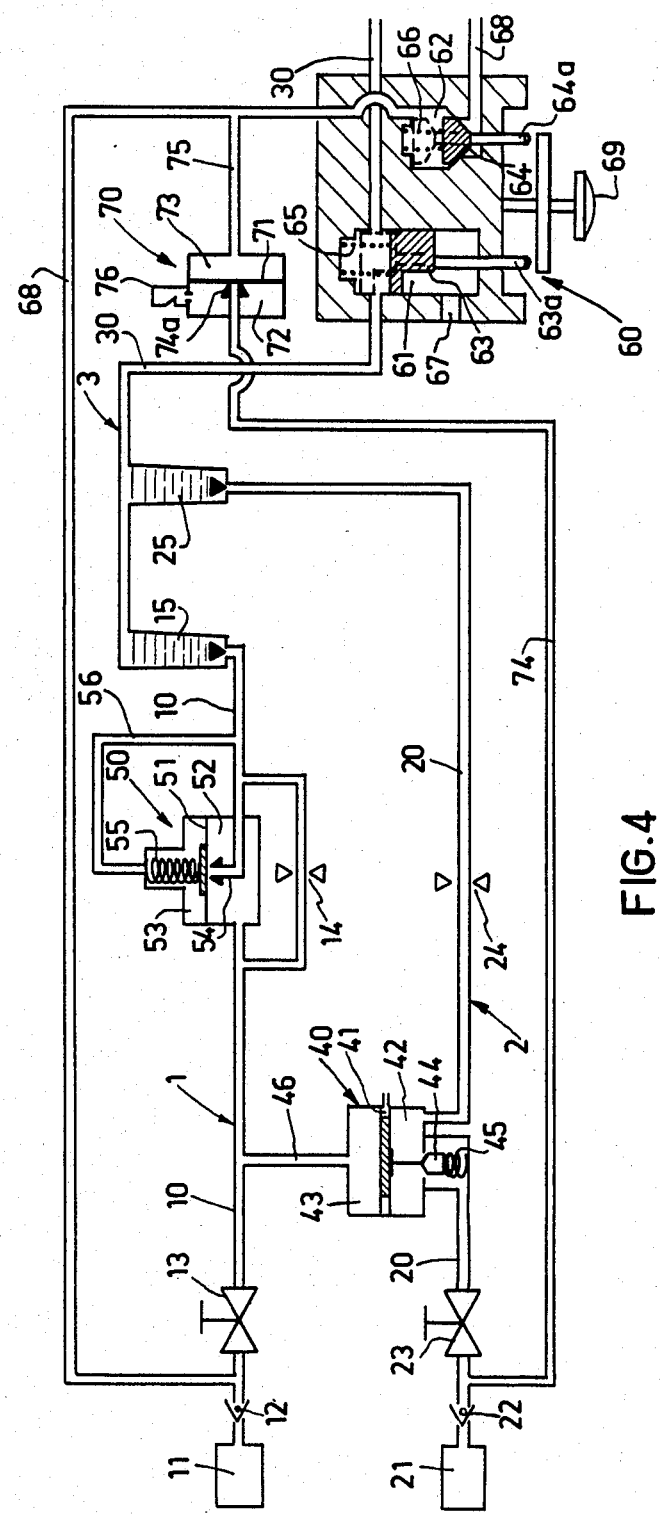

The embodiment of FIG. 4 is also provided with a warning device 70 comprising diaphragm 71 which divides it internally into two chambers 72 and 73 connected, respectively, to the source 21 of nitrous oxide via a pipe 74 the nozzle or bleed 74a of which is normally in contact with the said diaphragm and to the source 11 of oxygen via a pipe 75 which is itself connected to the aforesaid pipe 68. A whistle or the like 76 is in communication with the chamber 72. In normal operation, that is to say if the oxygen pressure is adequate, the diaphragm 71 is applied against the bleed 74a which is thus closed, whereas if the oxygen pressure drops below a particular value (for example 1 bar), the diaphragm 71 is separated from the bleed, the nitrous oxide passes through the whistle 76 which emits an audible signal and gives warning of the oxygen starvation.

Figure 5:
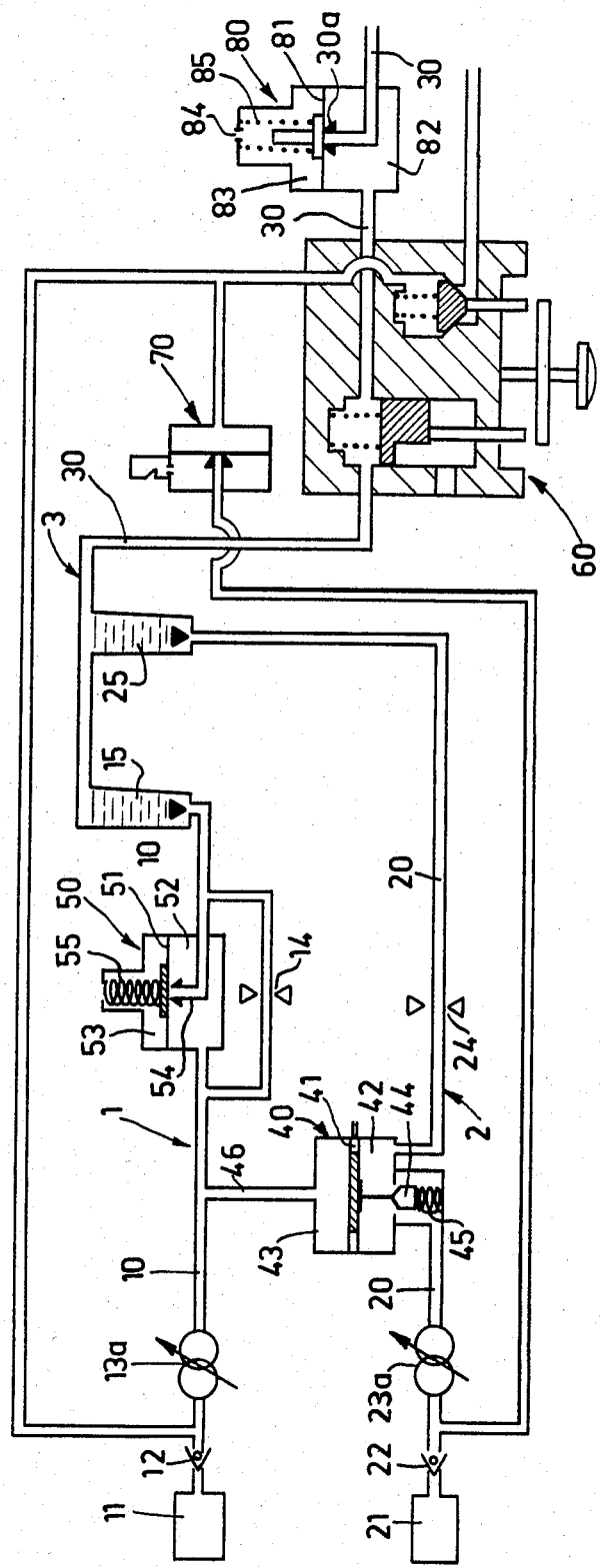

The appliances such as respirator masks, which are provides in the consumer circuit, feed in back pressures which have the result of falsifying the readings provided by the rotary flow-meters such as 15 and 25, these normally being calibrated at atmospheric pressure. The consequence is that the true rate of flow of the gas passing through a rotary flow-meter may differ substantially (for example being 1.2 times greater) from the rate of flow reading on this rotary flow-meter. The embodiment illustrated in FIG. 5 is provided with a release device 80 provided in the consumer circuit 3 downstream of the valve 60 and thus of the rotary flowmeters 15, 25 to eliminate this disadvantage. The release device 80 comprises a diaphragm 81 which divides it internally into a chamber 82 and a chamber 83 in communication with the outside through an orifice 84. The chamber 82 communicates with the pipe 30 of circuit 3, which pipe is provided with a nozzle or bleed 30a against which the diaphragm 81 is normally thrust by the action of a spring 85. The release device 80 is calibrated by means of the spring 85, in such manner that the pressure in the rotary flow-meters 15, 25 is kept constant irrespective of the back pressure in the consumer circuit. The rotary flow-meters should then be calibrated at the rated pressure of the release device (for example 500 mbar) and no longer at atmospheric pressure, and the rate of flow they indicate corresponds to the true rate of flow.

In the embodiment of FIG. 5, the circuits 1 and 2 are provided with adjustable pressure regulators 13a, 23a instead of with the cocks 13, 23 of the preceding embodiments, these pressure regulators permit stabilisation of the pressure of the flow of the said circuits irrespective of the fluctuations of the supply pressures. The release or expansion pressure of the pressure regulator 23a is preferably limited by design to a value such that the rate of flow of nitrous oxide is limited to a given value (for example 12 lites. min$^{-1}$), allowing for the resistance introduced by the calibrated orifice 24 and the constant pressure maintained in the rotary flowmeters 15, 25.

In this last case, the release device 50 of circuit 1 becomes useless because it has the purpose of limiting the rate of flow of nitrous oxide and may consequently be omitted.

Instead of being installed downstream of the valve 60 as shown in FIG. 5, the release device 80 could be installed directly downstream of the rotary flow-meters 15, 25.

It is pointed out that the application of pressure regulators and of the release device in the consumer circuit renders it possible to obtain a universal mixer, that is to say a mixer unaffected by the pressure fluctuations of the sources of gas, as well as by the back pressures of the consumer appliances.

Numerous modifications may be made in the embodiments described and illustrated, without thereby departing from the scope of the invention as defined by the appended claims.

I claim:

1. A mixer for delivering a mixture of a gas and a second gas in proportions of $X/100$ and $(100-X)/100$ respectively, comprising first and second circuits respectively connected to sources of said first and second gases, and delivering said first and second gases to flow-meter means, said first and second circuits respectively including first and second flow-rate control valves for independently controlling the flow rates of said first and second gases, and first and second calibrated orifices so calibrated that for an identical pressure of both cases, the rates of flow of said first and second gases through the first and second orifices are in the ratio of $X/(100-X)$, pressure limiting means connected between said first and second circuits, for limiting the pressure of the second gas to that of the first gas, and means connected in parallel with said first calibrated orifice for limiting to a constant value the pressure in the first circuit and consequently the pressure in the second circuit if the rate of flow of the first gas exceeds a predetermined value, the last-named means comprising a first chamber continuously communicating with said first circuit upstream from said first orifice and a diaphragm exposed to the action of a calibrated spring to open an outlet from said first chamber which is connected to said first circuit downstream from said first orifice only when the rate of flow of the first gas exceeds said predetermined value, and a second chamber in which said calibrated spring is housed, said second chamber being connected via a conduit to said first circuit downstream of said first chamber.

2. A mixer as claimed in claim 1, said pressure limiting means connected between said first and second circuits comprising a pressure limiter having a diaphragm controlling the operation of a valve in a conduit for said second gas, said diaphragm being exposed to the pressure of said first gas.

3. A mixer as claimed in claim 1, and a switching device having first and second chambers connected respectively to a consumer circuit and to said source of said first gas, and slide valves which as a function of their position allow a mixture of said gases to pass and simultaneously prevent passage of said first gas, or visa versa.

4. A mixer as claimed in claim 3, said valve having a push button acting against return spring means and allowing said valves to be controlled at the same time.

5. A mixer as claimed in claim 1, and a warning device connected to said sources of said first and second gases and adapted to issue a warning signal when the pressure of said first gas is lower than a predetermined value.

6. A mixer as claimed in claim 1, for delivering a mixture of oxygen and nitrous oxide for anaesthetic purposes, in which said calibrated orifices are calibrated such that for an identical pressure of the two gases, the rate of flow of nitrous oxide is no more than three times the rate of flow of oxygen.

* * * * *